(12) United States Patent
Geroy

(10) Patent No.: US 9,381,030 B2
(45) Date of Patent: Jul. 5, 2016

(54) TUNNELING TOOL FOR IMPLANTABLE LEADS

(75) Inventor: Jesse Geroy, Ham Lake, MN (US)

(73) Assignee: Nuvectra Corporation, Plano, TX (US)

( * ) Notice: Subject to any disclaimer, the term of this patent is extended or adjusted under 35 U.S.C. 154(b) by 516 days.

(21) Appl. No.: 13/046,144

(22) Filed: Mar. 11, 2011

(65) Prior Publication Data

US 2012/0016377 A1    Jan. 19, 2012

Related U.S. Application Data

(60) Provisional application No. 61/364,509, filed on Jul. 15, 2010.

(51) Int. Cl.
| A61B 19/00 | (2006.01) |
| A61B 17/32 | (2006.01) |
| A61B 17/00 | (2006.01) |
| A61N 1/05 | (2006.01) |

(52) U.S. Cl.
CPC .......... *A61B 17/320016* (2013.01); *A61B 2017/00946* (2013.01); *A61B 2017/320056* (2013.01); *A61N 1/0553* (2013.01)

(58) Field of Classification Search
CPC ........... A61B 19/201; A61B 2019/208; A61B 17/320016; A61B 2017/00946; A61B 2017/320056; A61N 2001/0578; A61N 1/056; A61N 1/0587; A61N 1/0553; Y10T 16/44; Y10T 16/469; Y10T 16/4713; B25G 1/00; B25G 3/00; B25G 3/02; B25G 3/04; B25G 3/12; B25G 3/14; B25G 3/16; B25G 3/18; B25G 3/20

USPC .................. 606/1, 159, 167, 129, 32–35, 41; 607/115; 600/16, 372–374
See application file for complete search history.

(56) References Cited

U.S. PATENT DOCUMENTS

| 3,630,192 | A | | 12/1971 | Jamshidi | |
| 3,779,658 | A | * | 12/1973 | Caperton | ................ F16B 7/182 403/339 |
| 3,915,174 | A | * | 10/1975 | Preston | .................. A61N 1/056 607/10 |
| 4,280,510 | A | * | 7/1981 | O'Neill | .......................... 607/131 |
| 4,574,806 | A | | 3/1986 | McCarthy | |
| 4,735,215 | A | * | 4/1988 | Goto et al. | .................... 600/567 |
| 4,793,363 | A | | 12/1988 | Ausherman et al. | |

(Continued)

OTHER PUBLICATIONS

International Search Report and Written Opinion, dated Nov. 2, 2011 for PCT/US2011/042926.

*Primary Examiner* — Amy R Weisberg
(74) *Attorney, Agent, or Firm* — Haynes and Boone, LLP; Erin Q. Li

(57) ABSTRACT

A tunneling tool for creating a pathway for implanting a therapy delivery element in a living body. The tunneling tool includes a malleable elongated shaft having a distal end. A sheath having a lumen is slidably positioned over a portion of the shaft. A primary handle secured to proximal end of the shaft permits a user to advance and manipulate the shaft and the sheath in the living body. A secondary handle with an opening is slidably positioned on the shaft between the primary handle and the sheath. The opening has a diameter less than an outside diameter of a proximal end of the sheath. A locking mechanism releasably engages the secondary handle to the primary handle. The sheath is retained in a desired location within the living body by securing the secondary handle relative to the living body as the primary handle is used to remove the shaft from the sheath.

20 Claims, 10 Drawing Sheets

(56) References Cited

U.S. PATENT DOCUMENTS

| | | | |
|---|---|---|---|
| 4,817,847 A | 4/1989 | Redtenbacher et al. | |
| 5,010,887 A * | 4/1991 | Thornander | A61N 1/3704 128/901 |
| 5,019,102 A | 5/1991 | Hoene | |
| 5,047,021 A * | 9/1991 | Utterberg | A61M 39/10 285/332 |
| 5,197,649 A | 3/1993 | Bessler et al. | |
| 5,279,570 A | 1/1994 | Dombrowski et al. | |
| 5,300,106 A * | 4/1994 | Dahl | A61N 1/05 604/164.05 |
| 5,306,240 A | 4/1994 | Berry | |
| 5,361,754 A | 11/1994 | Stuart | |
| 5,411,508 A | 5/1995 | Bessler et al. | |
| 5,496,345 A | 3/1996 | Kieturakis et al. | |
| 5,522,875 A * | 6/1996 | Gates | A61N 1/056 600/585 |
| 5,540,711 A | 7/1996 | Kieturakis et al. | |
| 5,607,443 A | 3/1997 | Kieturakis et al. | |
| 5,653,726 A | 8/1997 | Kieturakis | |
| 5,702,416 A | 12/1997 | Kieturakis et al. | |
| 5,728,133 A * | 3/1998 | Kontos | A61B 17/0057 128/887 |
| 5,778,877 A | 7/1998 | Stuart | |
| 5,782,841 A | 7/1998 | Ritz et al. | |
| 5,810,792 A * | 9/1998 | Fangrow, Jr. | A61M 39/045 285/319 |
| 5,817,123 A | 10/1998 | Kieturakis et al. | |
| 5,836,961 A | 11/1998 | Kieturakis et al. | |
| 5,944,732 A | 8/1999 | Raulerson et al. | |
| 6,004,337 A | 12/1999 | Kieturakis et al. | |
| 6,015,421 A | 1/2000 | Echeverry et al. | |
| 6,135,771 A * | 10/2000 | Dragan | A61C 5/062 433/90 |
| 6,168,608 B1 | 1/2001 | Echeverry et al. | |
| 6,264,604 B1 | 7/2001 | Kieturakis et al. | |
| 6,312,442 B1 | 11/2001 | Kieturakis et al. | |
| 6,315,184 B1 | 11/2001 | Whitman | |
| 6,360,750 B1 | 3/2002 | Gerber et al. | |
| 6,364,892 B1 | 4/2002 | Jervis | |
| 6,368,337 B1 | 4/2002 | Kieturakis et al. | |
| 6,378,400 B1 * | 4/2002 | Bogli | B25B 13/461 81/177.2 |
| 6,408,214 B1 * | 6/2002 | Williams | A61M 25/0041 607/122 |
| 6,432,121 B1 | 8/2002 | Jervis | |
| 6,443,973 B1 | 9/2002 | Whitman | |
| 6,475,244 B2 | 11/2002 | Herweck et al. | |
| 6,488,197 B1 | 12/2002 | Whitman | |
| 6,491,201 B1 | 12/2002 | Whitman | |
| 6,494,477 B1 * | 12/2002 | Parker | B60D 1/38 280/479.1 |
| 6,505,768 B2 | 1/2003 | Whitman | |
| 6,514,272 B1 | 2/2003 | Kieturakis et al. | |
| 6,517,565 B1 | 2/2003 | Whitman et al. | |
| 6,533,157 B1 | 3/2003 | Whitman | |
| 6,540,764 B1 | 4/2003 | Kieturakis et al. | |
| 6,562,056 B2 | 5/2003 | Jervis | |
| 6,565,590 B2 | 5/2003 | Kieturakis et al. | |
| 6,565,594 B1 | 5/2003 | Herweck et al. | |
| 6,592,602 B1 | 7/2003 | Peartree et al. | |
| 6,605,094 B1 | 8/2003 | Mann et al. | |
| 6,632,234 B2 | 10/2003 | Kieturakis et al. | |
| 6,669,691 B1 * | 12/2003 | Taimisto | A61B 18/1482 606/41 |
| 6,671,554 B2 * | 12/2003 | Gibson | A61N 1/05 439/827 |
| 6,679,900 B2 | 1/2004 | Kieturakis et al. | |
| 6,681,979 B2 | 1/2004 | Whitman | |
| 6,695,856 B2 | 2/2004 | Kieturakis et al. | |
| 6,698,643 B2 | 3/2004 | Whitman | |
| 6,716,230 B2 | 4/2004 | Whitman | |
| 6,716,233 B1 | 4/2004 | Whitman | |
| 6,755,845 B2 | 6/2004 | Kieturakis et al. | |
| 6,758,853 B2 | 7/2004 | Kieturakis et al. | |
| 6,793,652 B1 | 9/2004 | Whitman et al. | |
| 6,836,917 B2 * | 1/2005 | Blaustein | A61C 17/34 15/22.1 |
| 6,843,403 B2 | 1/2005 | Whitman | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,866,676 B2 | 3/2005 | Kieturakis et al. | |
| 6,936,052 B2 | 8/2005 | Gellman et al. | |
| 6,953,467 B2 | 10/2005 | Kieturakis et al. | |
| 6,971,393 B1 * | 12/2005 | Mamo | A61N 1/0551 128/898 |
| 6,981,941 B2 | 1/2006 | Whitman et al. | |
| 6,991,597 B2 | 1/2006 | Gellman et al. | |
| 7,001,405 B2 | 2/2006 | Kieturakis et al. | |
| 7,018,384 B2 | 3/2006 | Skakoon | |
| 7,025,772 B2 | 4/2006 | Gellman et al. | |
| 7,032,798 B2 | 4/2006 | Whitman et al. | |
| 7,074,213 B2 | 7/2006 | McGuckin, Jr. et al. | |
| 7,077,829 B2 | 7/2006 | McGuckin, Jr. et al. | |
| 7,077,856 B2 | 7/2006 | Whitman | |
| 7,097,635 B2 | 8/2006 | McGuckin, Jr. et al. | |
| 7,114,642 B2 | 10/2006 | Whitman | |
| 7,120,499 B2 | 10/2006 | Thrope et al. | |
| 7,179,272 B2 | 2/2007 | Kieturakis et al. | |
| 7,204,831 B2 | 4/2007 | McGuckin, Jr. et al. | |
| 7,214,236 B2 | 5/2007 | Kieturakis et al. | |
| 7,218,970 B2 | 5/2007 | Ley et al. | |
| 7,235,043 B2 | 6/2007 | Gellman et al. | |
| 7,297,153 B2 | 11/2007 | Kieturakis et al. | |
| 7,300,448 B2 | 11/2007 | Criscuolo et al. | |
| 7,316,667 B2 * | 1/2008 | Lindstrom | A61B 17/3468 604/164.05 |
| 7,338,092 B1 * | 3/2008 | Cicconi, III | F16L 37/144 285/1 |
| 7,343,202 B2 * | 3/2008 | Mrva | A61N 1/0524 607/116 |
| 7,369,901 B1 * | 5/2008 | Morgan | A61N 1/059 600/375 |
| 7,389,138 B2 * | 6/2008 | Wagner | A61N 1/36585 607/10 |
| 7,390,322 B2 | 6/2008 | McGuckin, Jr. et al. | |
| 7,537,602 B2 | 5/2009 | Whitman | |
| 7,565,198 B2 | 7/2009 | Bennett et al. | |
| 7,566,316 B2 | 7/2009 | McGuckin, Jr. et al. | |
| 7,628,795 B2 | 12/2009 | Karwoski et al. | |
| 7,641,688 B2 | 1/2010 | Lesh | |
| 7,695,485 B2 | 4/2010 | Whitman et al. | |
| 7,695,487 B2 | 4/2010 | Peartree et al. | |
| 7,726,994 B1 * | 6/2010 | Willey | A42B 3/042 439/218 |
| 7,743,960 B2 | 6/2010 | Whitman et al. | |
| 7,758,613 B2 | 7/2010 | Whitman | |
| 7,792,591 B2 | 9/2010 | Rooney | A61M 25/0662 604/104 |
| 7,799,014 B2 | 9/2010 | McGuckin, Jr. et al. | |
| 7,894,913 B2 * | 2/2011 | Boggs | A61N 1/36107 607/118 |
| 8,224,453 B2 * | 7/2012 | De Ridder | A61N 1/36071 607/117 |
| 8,233,992 B2 * | 7/2012 | Zhu | A61N 1/0553 607/117 |
| 2001/0018549 A1 * | 8/2001 | Scetbon | A61B 17/0469 600/30 |
| 2003/0070726 A1 * | 4/2003 | Andreasson | A61J 1/2096 141/329 |
| 2004/0018764 A1 * | 1/2004 | Thurston | H01R 13/623 439/312 |
| 2004/0176781 A1 * | 9/2004 | Lindstrom | A61B 17/3468 606/129 |
| 2005/0033268 A1 * | 2/2005 | Decaria | A61M 39/10 604/533 |
| 2005/0131391 A1 | 6/2005 | Chu et al. | |
| 2006/0079769 A1 * | 4/2006 | Whiting | A61M 25/0041 600/434 |
| 2006/0149345 A1 * | 7/2006 | Boggs, II | A61N 1/0556 607/118 |
| 2007/0173879 A1 | 7/2007 | Pandey | |

(56) References Cited

U.S. PATENT DOCUMENTS

| | | | |
|---|---|---|---|
| 2007/0243013 A1* | 10/2007 | Hewitt | B25G 3/18 403/351 |
| 2008/0009749 A1 | 1/2008 | Delianides et al. | |
| 2008/0058853 A1 | 3/2008 | Kieturakis et al. | |
| 2008/0103572 A1* | 5/2008 | Gerber | A61N 1/0529 607/116 |
| 2008/0119846 A1* | 5/2008 | Rioux | A61B 18/1477 606/41 |
| 2008/0132969 A1* | 6/2008 | Bennett | A61N 1/0558 607/41 |
| 2008/0154296 A1 | 6/2008 | Taylor et al. | |
| 2008/0281228 A1* | 11/2008 | Parodi | A61M 25/09 600/585 |
| 2008/0312677 A1 | 12/2008 | Massengale et al. | |
| 2009/0030444 A1 | 1/2009 | Pandey et al. | |
| 2009/0157091 A1* | 6/2009 | Buysman | A61N 1/36017 606/129 |
| 2009/0157927 A1 | 6/2009 | Rofougaran | |
| 2009/0240258 A1 | 9/2009 | Kuzma et al. | |
| 2009/0254095 A1 | 10/2009 | Levine et al. | |
| 2010/0125194 A1* | 5/2010 | Bonner | A61B 5/0538 600/424 |
| 2010/0137879 A1* | 6/2010 | Ko | A61M 25/0668 606/129 |
| 2010/0292724 A1* | 11/2010 | Ravikumar | A61B 17/221 606/185 |
| 2010/0324570 A1* | 12/2010 | Rooney | A61M 25/0662 606/129 |
| 2010/0324579 A1* | 12/2010 | Bardy | A61M 37/0069 606/167 |
| 2010/0331925 A1* | 12/2010 | Peterson | A61N 1/36071 607/72 |
| 2011/0257660 A1* | 10/2011 | Jones | A61B 17/3415 606/129 |
| 2011/0257709 A1* | 10/2011 | Ackermann | A61N 1/0551 607/62 |
| 2011/0270268 A1* | 11/2011 | Eversull | A61M 39/10 606/129 |
| 2012/0029335 A1* | 2/2012 | Sudam | A61N 1/05 600/374 |
| 2012/0071956 A1* | 3/2012 | Stevenson | A61B 18/1492 607/117 |
| 2012/0191106 A1* | 7/2012 | Ko | A61M 25/0668 606/129 |
| 2012/0197370 A1* | 8/2012 | Kim | A61N 1/0558 607/118 |
| 2012/0209285 A1* | 8/2012 | Barker | A61B 17/3468 606/129 |
| 2012/0245594 A1* | 9/2012 | Jones | A61B 17/3415 606/129 |
| 2012/0290055 A1* | 11/2012 | Boggs, II | A61N 1/36071 607/116 |
| 2013/0158564 A1* | 6/2013 | Harris | A61B 17/3401 606/129 |

\* cited by examiner

TUNNELING TOOL FOR IMPLANTABLE LEADS

RELATED APPLICATIONS

The present application claims the benefit of U.S. Provisional Application Ser. No. 61/364,509, entitled TUNNELING TOOL TWO-PIECE HANDLE, filed Jul. 15, 2010, the entire disclosures of which are hereby incorporated by reference.

FIELD

The present disclosure relates to tunneling tool for implanting therapy delivery elements, such as stimulation leads or catheters, within a living body. The tunneling tool includes a primary handle used to pull the shaft out of the living body, while a secondary handle retains an outer sheath on the shaft in the living body.

BACKGROUND

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Peripheral Nerve Stimulation (PNS) systems have demonstrated efficacy in the treatment of chronic pain syndromes and incontinence, and a number of additional applications are currently under investigation. Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes one or more therapy delivery elements implanted at the desired stimulation site and an implantable neurostimulator, such as an implantable pulse generator (IPG), implanted remotely from the stimulation site, but coupled either directly to the therapy delivery elements or indirectly to the therapy delivery elements via one or more extensions in cases where the length of the therapy delivery elements is insufficient to reach the IPG. In some cases, the extension leads may be used to facilitate coupling of the neurostimulator, which may otherwise be incompatible with the therapy delivery elements or extension leads, thereto. Thus, electrical pulses can be delivered from the neurostimulator to the therapy delivery elements to stimulate the tissue and provide the desired efficacious therapy to the patient.

In the context of an SCS procedure, one or more therapy delivery elements are introduced through the patient's back into the epidural space under fluoroscopy, such that the electrodes carried by the leads are arranged in a desired pattern and spacing to create an electrode array. The specific procedure used to implant the therapy delivery elements will ultimately depend on the type of therapy delivery elements used.

Currently, there are two types of commercially available therapy delivery elements: a percutaneous lead and a surgical lead.

A percutaneous lead includes a cylindrical body with ring electrodes, and can be introduced into contact with the affected spinal tissue through a Touhy-like needle, which passes through the skin, between the desired vertebrae, and into the epidural space above the dura layer. For unilateral pain, a percutaneous lead is placed on the corresponding lateral side of the spinal cord. For bilateral pain, a percutaneous lead is placed down the midline of the spinal cord, or two percutaneous leads are placed down the respective sides of the midline. In many cases, a stylet, such as a metallic wire, is inserted into a lumen running through the center of each of the percutaneous leads to aid in insertion of the lead through the needle and into the epidural space. The stylet gives the lead rigidity during positioning, and once the lead is positioned, the stylet can be removed after which the lead becomes flaccid.

A surgical lead has a paddle on which multiple electrodes are arranged in independent columns, and is introduced into contact with the affected spinal tissue using a surgical procedure, and specifically, a laminectomy, which involves removal of the laminar vertebral tissue to allow both access to the dura layer and positioning of the lead.

After proper placement of the therapy delivery elements at the target area of the spinal cord, the therapy delivery elements are anchored in place at an exit site to prevent movement. To facilitate the location of the implantable pulse generator away from the exit point of the therapy delivery elements, extension leads are sometimes used. In particular, the proximal ends of the therapy delivery elements, which include terminals respectively coupled to the electrodes on the therapy delivery elements, are inserted into connectors located at the distal ends of extension leads.

The proximal ends of the therapy delivery elements exiting the spinal column, or alternatively extension leads, are passed through a tunnel or pathway formed subcutaneously along the torso of the patient to a subcutaneous pocket (typically made in the patient's abdominal or buttock area) where a implantable pulse generator is implanted. The subcutaneous pathway can be formed using a tunneling tool over which a sheath may be threaded.

The tunneling tool is often bent to a desired shape of the subcutaneous tunnel. The tunneling tool is then removed to permit the therapy delivery elements to be threaded through the sheath. The bends in the tunneling tool, however, often interfere with separation of the tunneling tool from the sheath.

BRIEF SUMMARY

The present disclosure relates to tunneling tool for implanting therapy delivery elements, such as stimulation leads or catheters, within a living body. The tunneling tool includes a primary handle used to pull the shaft out of the living body, while a secondary handle retains an outer sheath on the shaft in the living body.

The tunneling tool is used to create a pathway for implanting a therapy delivery element in a living body. The tunneling tool includes a malleable elongated shaft having a distal end. A sheath having a lumen is slidably positioned over a portion of the shaft. A primary handle secured to proximal end of the shaft permits a user to advance and manipulate the shaft and the sheath in the living body. A secondary handle with an opening is slidably positioned on the shaft between the primary handle and the sheath. The opening has a diameter less than an outside diameter of a proximal end of the sheath, so that the secondary handle abuts, but is not attached to, the sheath.

In one embodiment, a locking mechanism releasably engages the secondary handle to the primary handle. The sheath is retained in a desired location within the living body by securing the secondary handle relative to the living body as the primary handle is used to remove the shaft from the sheath.

The proximal end of the sheath is preferably releasably attached to the secondary handle. In one embodiment, the locking mechanism includes a protrusion with at least one recess formed at a distal end of the primary handle. A recess in the proximal end of the secondary handle is sized to fit over the protrusion. The recess includes at least one tab sized to releasably engage with a recess in the protrusion in a locked position. The tabs preferably engage with the recess on the protrusion with a twisting-lock motion.

The present disclosure is also directed to a neurostimulation system including an implantable pulse generator and a therapy delivery element. The therapy delivery element includes a proximal end adapted to electrically couple with the implantable pulse generator and a distal end with a plurality of electrodes electrically coupled to the implantable pulse generator. An anchor is provided for securing the therapy delivery element in a desired location within a living body. The present tunneling tool is used to create a pathway for implanting the therapy delivery element in a living body. The sheath is retained in a desired location within the living body by securing the secondary handle as the primary handle is used to remove the shaft from the sheath.

The present disclosure is also directed to a method of creating a pathway for implanting a therapy delivery element in a living body. The method includes the steps of inserting distal end of a tunneling tool between skin and muscle tissue in the living body to create the pathway. A primary handle of the tunneling tool is disengaged from a secondary handle. The secondary handle engages with proximal end of a flexible sheath positioned on shaft of the tunneling tool. The secondary handle is retained relative to the living body to secure the flexible sheath located in the pathway, as the primary handle is used to remove the shaft of tunneling tool from the flexible sheath. The secondary handle is then separated from the flexible sheath. The therapy delivery element is passed through the flexible sheath. Finally, the flexible sheath is removed from the pathway. The shaft is typically shaped in a non-linear configuration before inserting into the living body.

The present disclosure is also directed to a method of implanting a neurostimulation system within a living body. The method includes the step of positioning electrodes at distal end of a therapy delivery element through a first incision site to a target location within the living body. Proximal end of the therapy delivery elements is accessible through the first incision site. The therapy delivery element is attached to the living body. A subcutaneous pocket is formed for implanting an implantable pulse generator within the living body at a second incision site. Distal end of a tunneling tool is inserted between skin and muscle tissue in the living body to create the pathway between the first and second incisions. The primary handle is disengaged from a secondary handle of the tunneling tool. The secondary handle engages with proximal end of a flexible sheath positioned on shaft of the tunneling tool. The secondary handle is retained relative to the living body to secure the flexible sheath along the pathway, while the primary handle is grasped to remove the shaft of tunneling tool from the flexible sheath. The secondary handle is separated from the flexible sheath. The therapy delivery element is passed through the flexible sheath. The flexible sheath is then removed from the pathway, leaving the therapy delivery element in the living body. The proximal end of the therapy delivery element is electrically coupled to the implantable pulse generator.

DETAILED DESCRIPTION OF SOME EMBODIMENTS

The description that follows relates to a spinal cord stimulation (SCS) system. However, it is to be understood that the while the present disclosure lends itself well to applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be an electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, any combination thereof "Target tissue site" refers generally to the target site for implantation of a therapy delivery element, regardless of the type of therapy.

Figure 1:
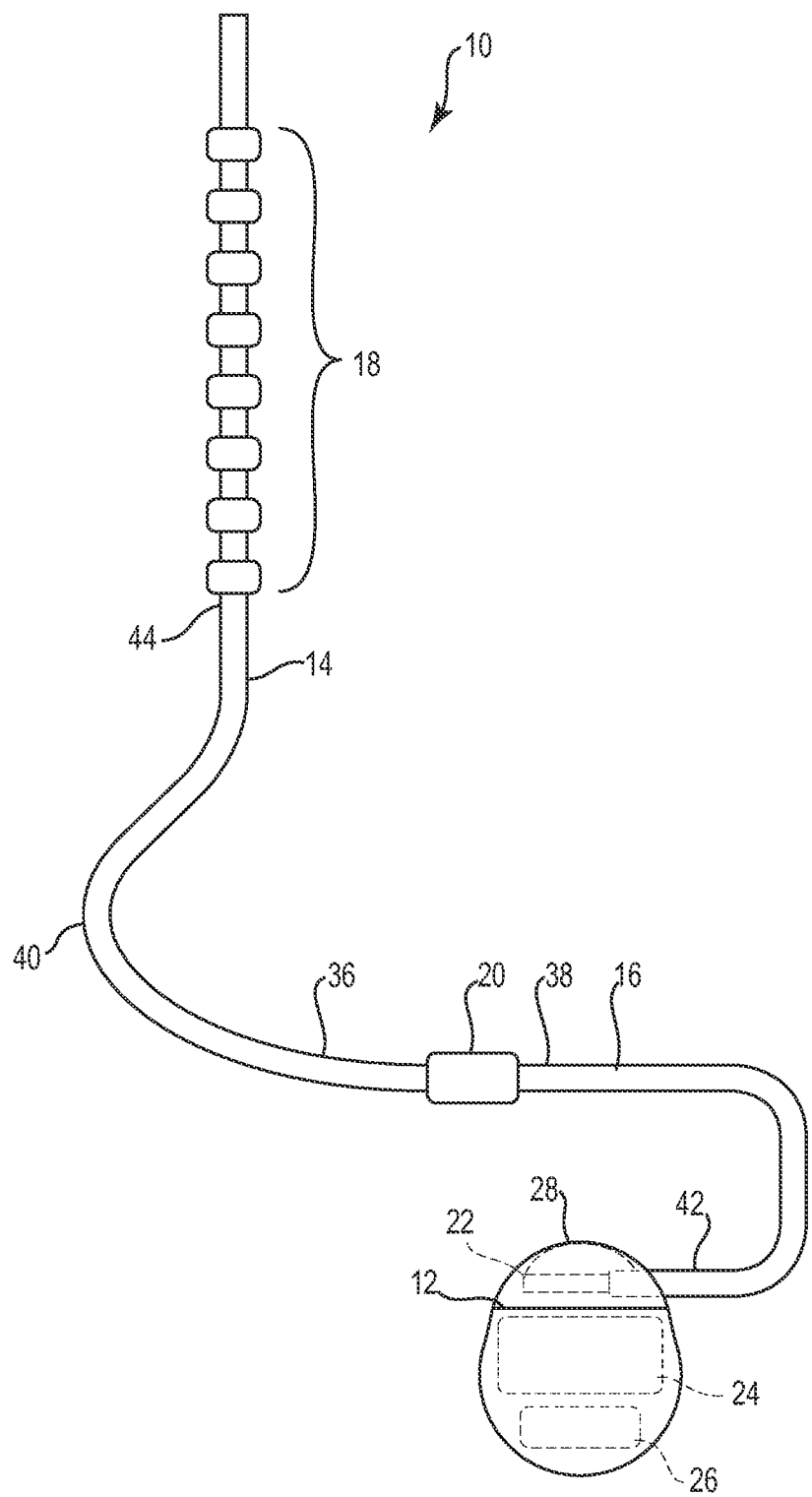
FIG. 1 is a schematic illustration of a therapy delivery system.

FIG. 1 illustrates a generalized therapy delivery system 10 that may be used in spinal cord stimulation (SCS), as well as other stimulation applications. The therapy delivery system 10 generally includes an implantable pulse generator 12, an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10.

The therapy delivery element 14 includes elongated body 40 having a proximal end 36 and a distal end 44. The elongated body 40 typically has a diameter of between about 0.03 inches to 0.07 inches and a length within the range of 30 cm to 90 cm for spinal cord stimulation applications. The elongated body 40 may be composed of a suitable electrically insulative material, such as, a polymer (e.g., polyurethane or silicone), and may be extruded from as a unibody construction.

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 20.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 are protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2:
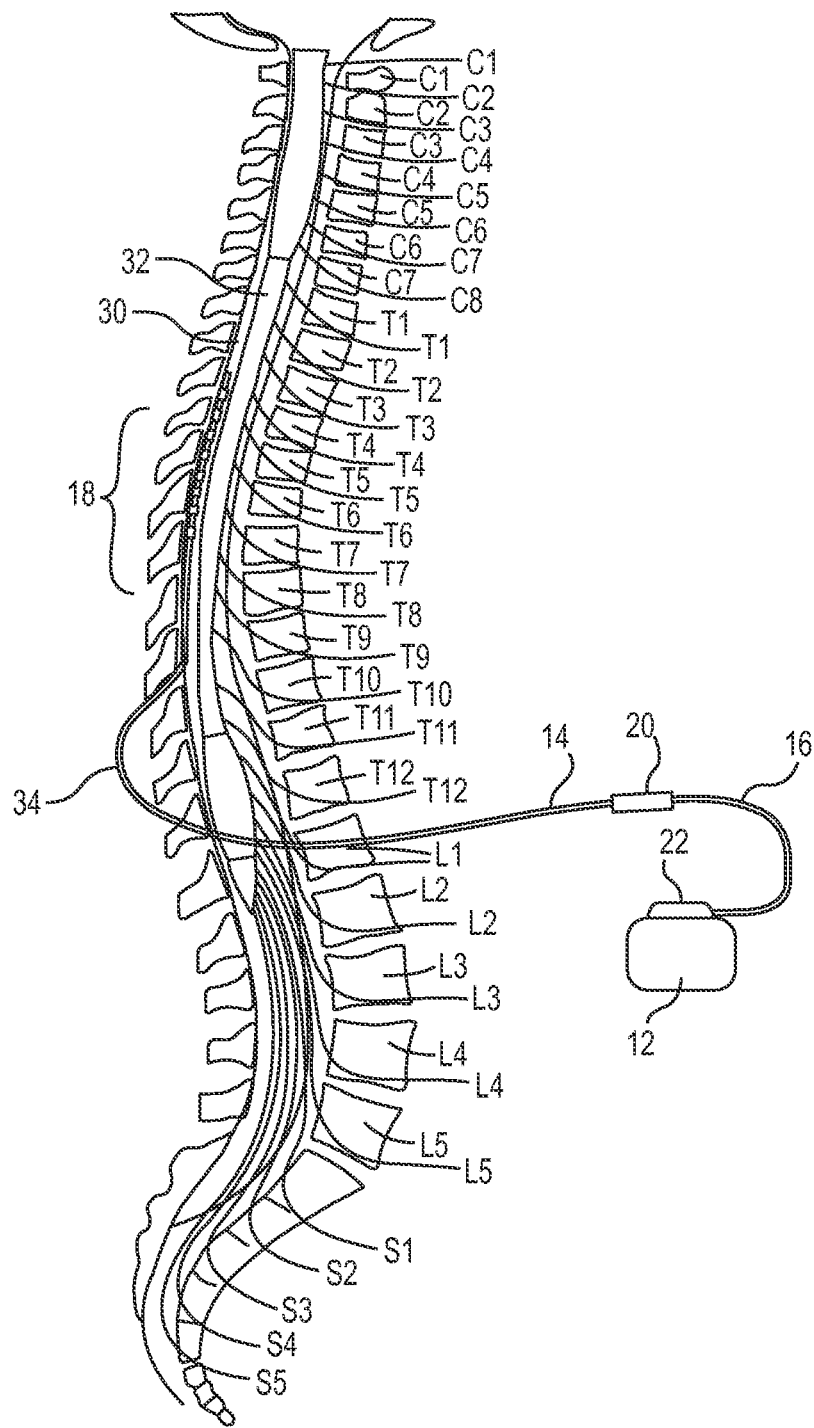
FIG. 2 is a schematic illustration of an environment for a therapy delivery system in accordance with an embodiment of the present disclosure.

FIG. 2 illustrates the therapy delivery element 14 implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as for example proximate the sacral nerves.

Figure 3:
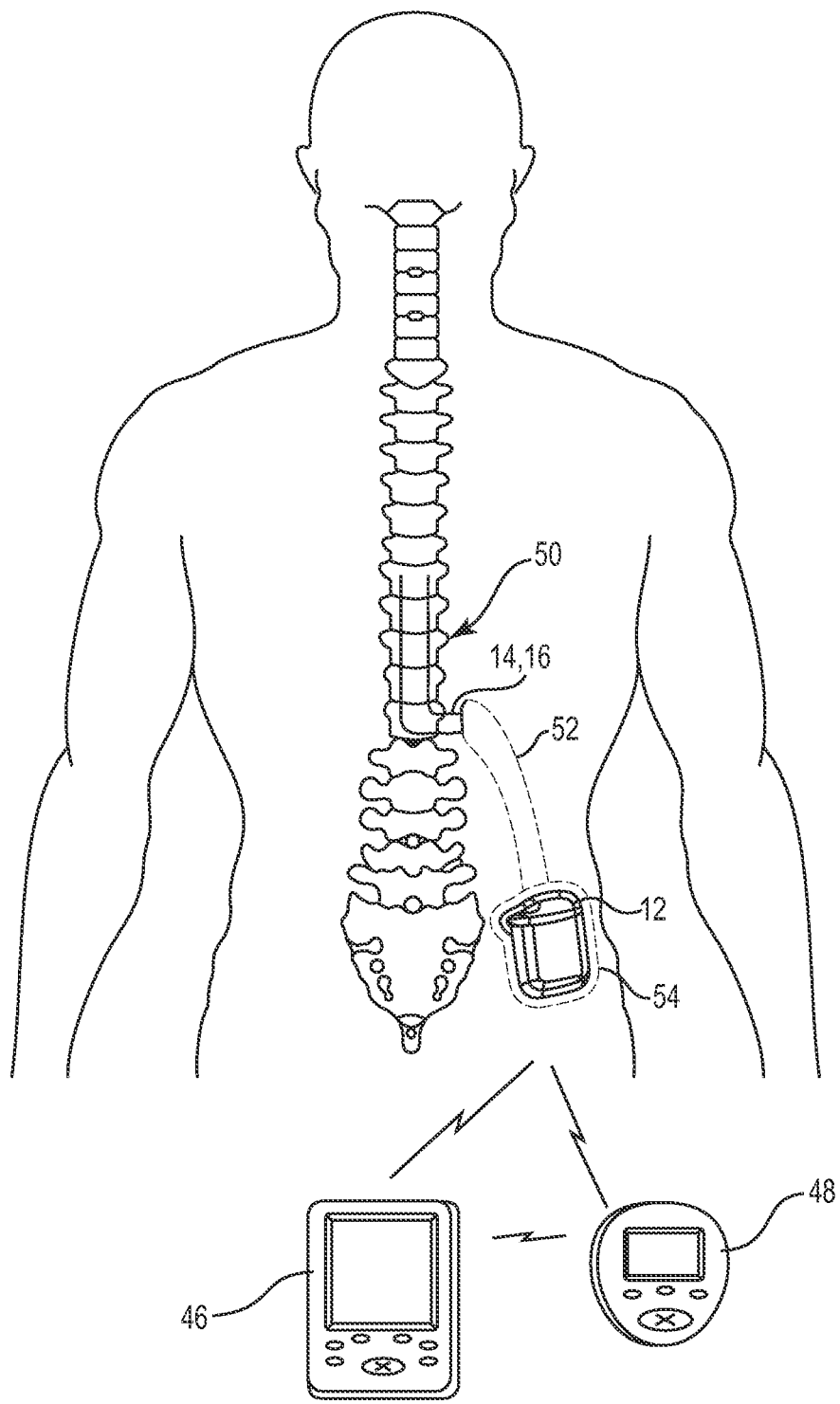
FIG. 3 is an alternate illustration of the environment for an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 3. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 3, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 48, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

FIG. 3 also illustrates a general environmental that may benefit from use of a tunneling tool in accordance with an embodiment of the present disclosure. Since the implantable pulse generator 12 is located remotely from target location 50 for therapy, the therapy delivery element 14 and/or the extension lead 16 is typically routed through a pathways 52 subcutaneously formed along the torso of the patient to a subcutaneous pocket 54 where the implantable pulse generator 12 is located.

Figure 4:
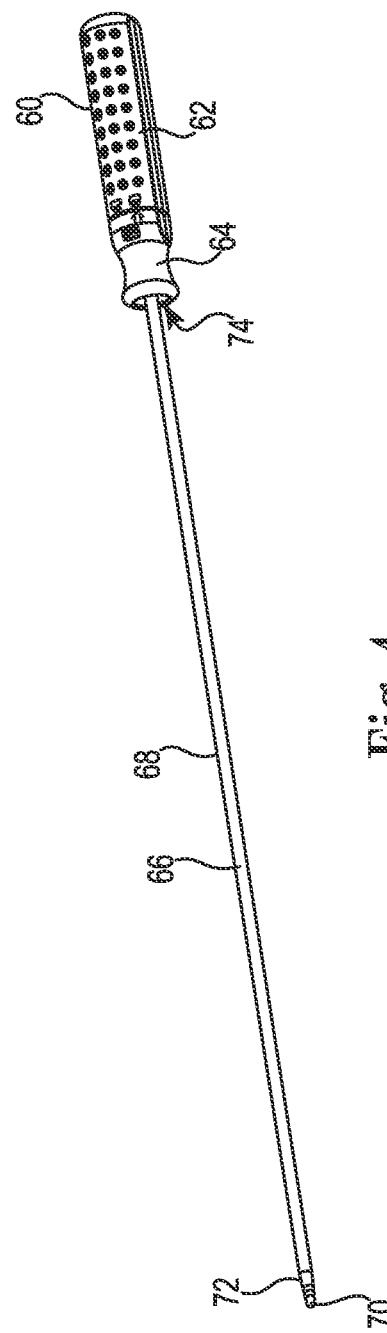
FIG. 4 is a perspective view of a tunneling tool with a two-part handle in accordance with an embodiment of the present disclosure.

FIG. 4 is a perspective view of tunneling tool 60 for creating such pathways, such as the pathway 52 of FIG. 3, to rough implantable therapy delivery elements 14 and/or lead extension 16 subcutaneously from the target stimulation site 50 to the implantable implantable pulse generator 12, in accordance with an embodiment of the present disclosure. The tunneling tool 60 includes primary handle 62, secondary handle 64, malleable shaft 66, and flexible sheath 68. Distal end 70 of the shaft 66 preferably protrudes beyond distal end 72 of the flexible sheath 68 to bore through subcutaneous tissue. Proximal end 74 of the sheath 68 is engaged with, but not attached to, the secondary handle 64.

The malleable shaft 66 permits the surgeon to customize the shape of the tunneling device 60 prior to and/or during insertion of the tunneling device into the anatomy. The shape of the malleable shaft 66 may be more or less intricate, as may be required by a particular procedure. The malleable shaft 66 is preferably made of a bendable or flexible material such as stainless steel or titanium or any other suitable material or combination of materials. The malleable shaft 66 may be any suitable size in shape and is generally sized to be slightly smaller than the size or diameter of a cable or wire connected to an implant device, which is routed through a person's body. The flexible sheath 68 is preferably constructed from a fluoropolymer material.

Figure 5:
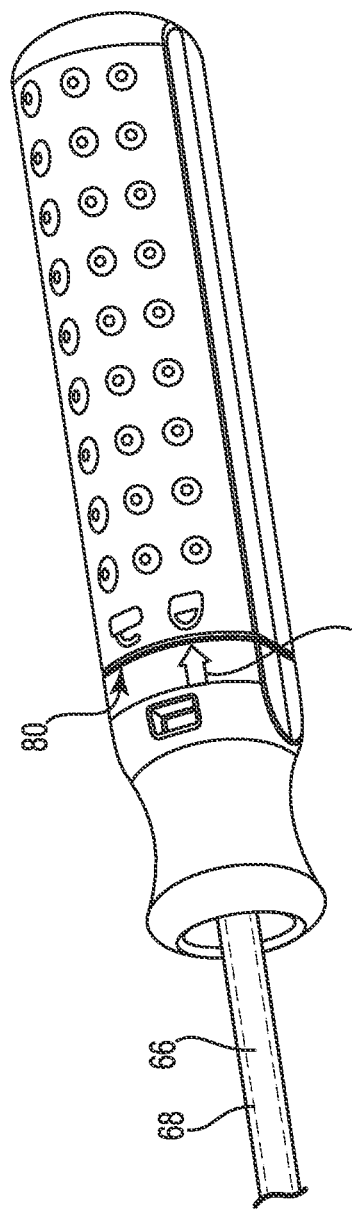
FIG. 5 is a perspective view of the tunneling tool of FIG. 4 with the two-part handle in a locked position in accordance with an embodiment of the present disclosure.
Figure 6:
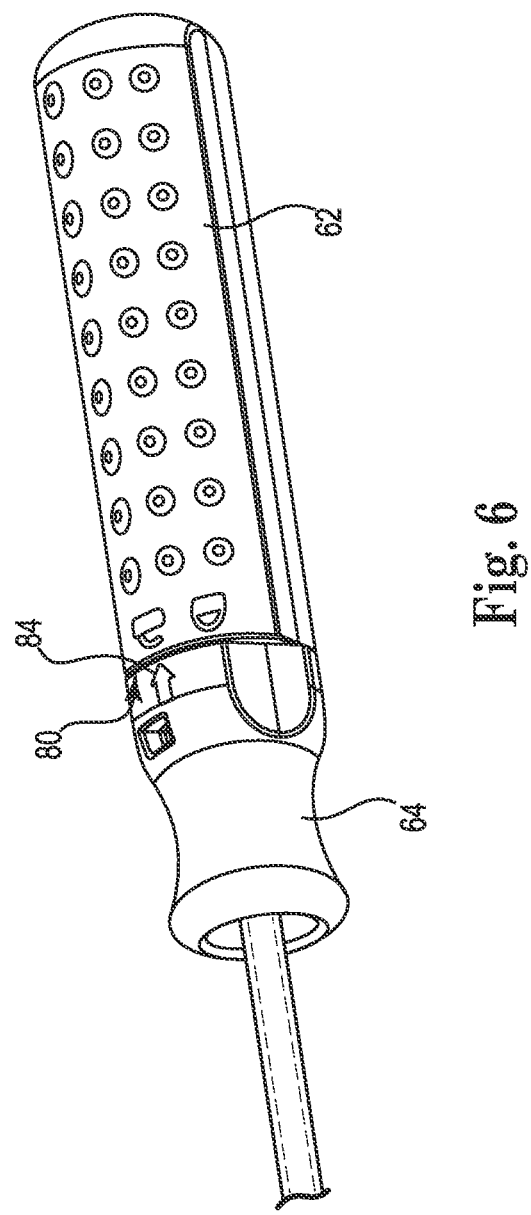
FIG. 6 is a perspective view of the tunneling tool of FIG. 4 with the two-part handle in an unlocked position in accordance with an embodiment of the present disclosure.

FIGS. 5 and 6 illustrate operation of locking mechanism 80 that connects the secondary handle 64 to the primary handle 62 in accordance with an embodiment of the present disclosure. In the illustrated embodiment, the locking mechanism 80 is a twist-lock structure. FIG. 5 illustrates the handles 62, 64 in locked position 82 and FIG. 6 illustrates unlocked position 84. The locking mechanism 80 secures the two handles 62, 64 together and allows them to easily separate. The optional locking mechanism facilitates gripping both the primary and secondary handles 62, 64 while inserting the distal end 70 into the patient.

Figure 7:
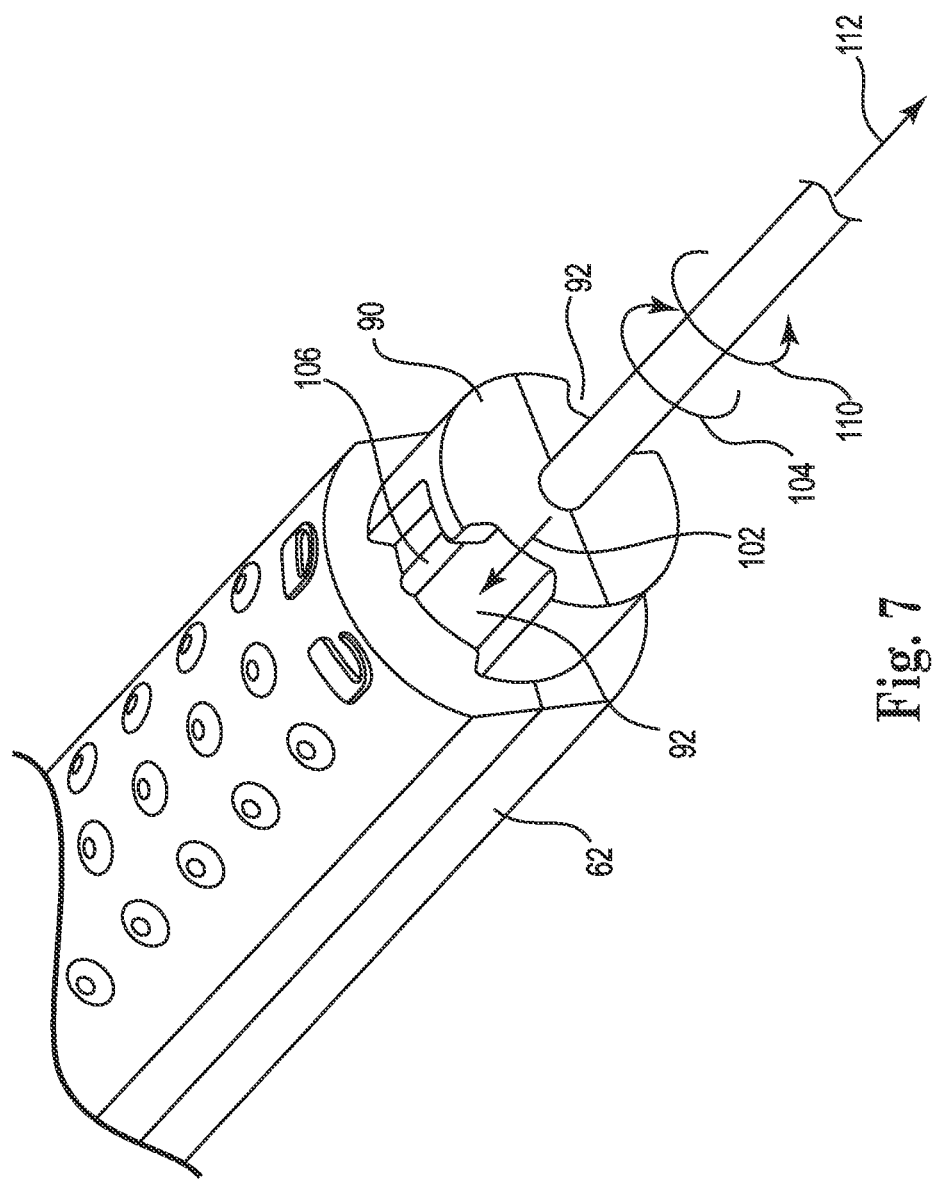
FIG. 7 is a perspective view of a locking mechanism on a primary handle of FIG. 4.
Figure 8:
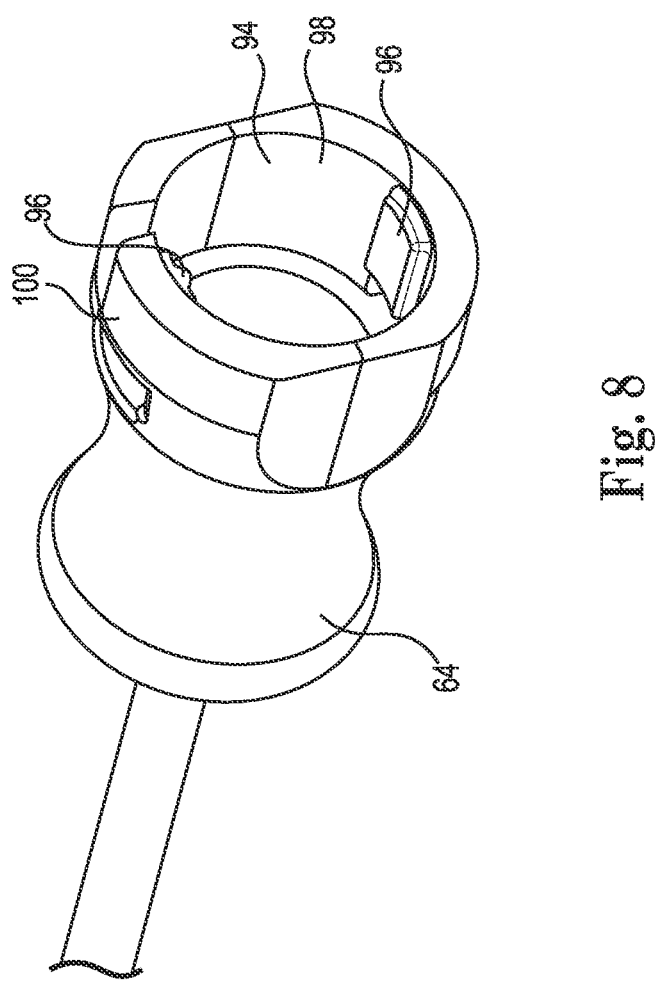
FIG. 8 is a perspective view of a locking mechanism on the secondary handle of FIG. 4.

FIGS. 7 and 8 are perspective views of the locking mechanism 80 in accordance with an embodiment of the present disclosure. Primary handle 62 includes protrusion 90 with one or more recesses 92. Secondary handle 64 include recess 94 sized to fit over the protrusion 90. Tabs 96 formed along inside diameter 98 of the recess 94 are sized to interlock with the recesses 92 on the primary handle 62. In the preferred embodiment, the tabs 96 are located on cantilevered arms 100 molded in the secondary handle 64.

In operation, the tabs 96 are advanced into recesses 92 in direction 102. The secondary handle 64 is then rotated in direction 104, so that the tabs 96 slide over locking ridges 106 located in the recesses 9. The locking ridges 106 retain the handles 62, 66 in the locked position 82. In the preferred embodiment, the cantilevered arms 100 flex to permit the tabs 96 to pass over the locking ridges 106.

The secondary handle 64 is separated from the primary handle 62 using the reverse process. The secondary handle 64 is first rotated in direction 110 to shift the tabs 96 to the opposite side of the locking ridges 106. The secondary handle 64 is then moved in direction 112, parallel to the shaft 66.

Figure 9:
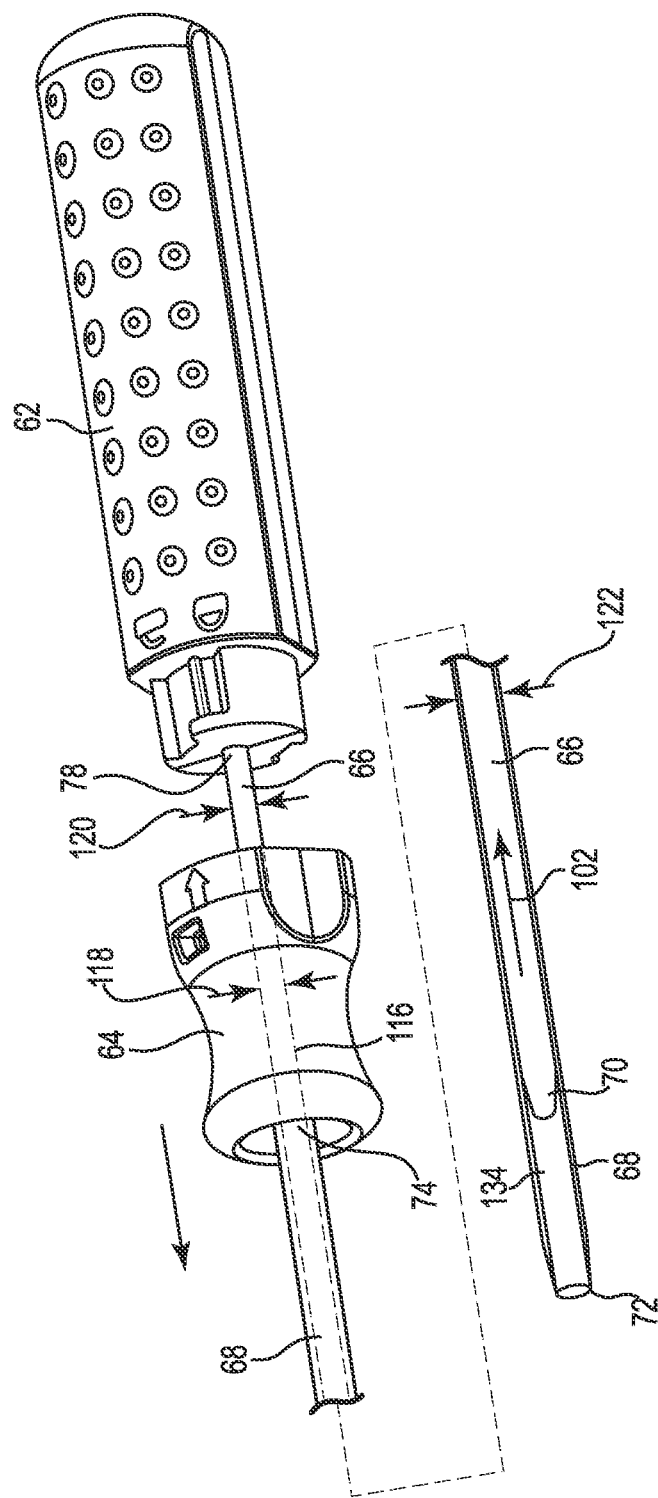
FIG. 9 is a perspective view of the secondary handle advancing a sheath on the tunneling tool of FIG. 4 in accordance with an embodiment of the present disclosure.

FIG. 9 illustrates the secondary handle 64 separated from the primary handle 62 and advanced along the shaft 66 in direction 112. Proximal end 78 of the shaft 66 is fixedly secured to the primary handle 62. The proximal end 74 of the sheath 68 abuts, but is not attached to, the secondary handle 64. The secondary handle 64 includes an opening 116 with diameter 118 that is greater than outside diameter 120 of the shaft 66. The diameter 118 of the opening, however, is less than outside diameter 122 of the sheath 68, so the sheath 68 advanced along the shaft 66 as the secondary handle 64 moves in the direction 112. As the secondary handle 64 is advanced in the direction 112, the shaft 66 is retracted from the sheath 68 in direction 102.

In operation, the distal end 70 of the shaft 66 is inserted into an incision of a patient. The shaft 66 can be inserted at an incision site near the therapy delivery element 14 or an incision site near the implantable pulse generator 12 is located, or an intermediate location between the two.

Once the tunneling device 60 has been inserted under the skin, it is directed, usually between the skin and muscle tissue, to the target region within the body. Preferably, the distal end 70 of the shaft 66 is blunt in order to inhibit damage to sensitive tissue such as nerves. For example, the blunt distal end minimizes coring of tissue as the tunneling device 60 is moved through the anatomy.

The shaft 66 and sheath 68 may be bent by the surgeon, either before or during insertion, to facilitate forming the pathway 52 to the desired location. The distal end 70 of the shaft 66 bores through the tissue to the desired target site by the force of the surgeon pushing the tool 60 into the patient.

Once the distal end 70 of the shaft 66 and distal end 72 of the sheath 68 are at the target location, the surgeon rotates the secondary handle 64 in direction 110 to separate the two handles 62, 64. The surgeon grasps the handle 62 to withdraw the shaft 66 from the patient, while simultaneously holding the secondary handle 64 to maintain the sheath 68 in the desired location within the pathway 52. The shaft 66 is completely removed from the sheath 68, leaving the hollow sheath 68 in place inside the patient. The secondary handle 64 is separated from the sheath 68.

Figure 10:
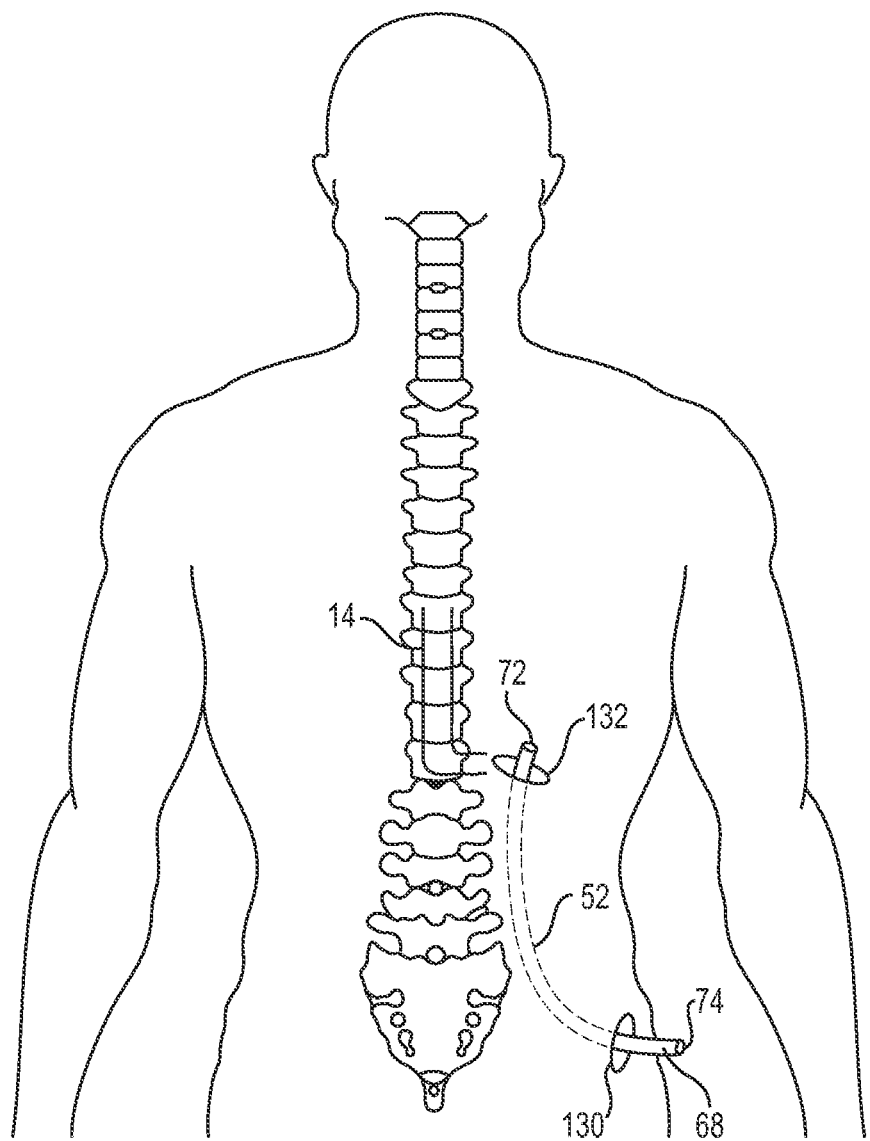
FIG. 10 is a schematic illustration of a sheath located in a patient in accordance with an embodiment of the present disclosure.

FIG. 10 illustrates the sheath 68 extending into the patient along the pathway 52, with the shaft 66 removed. The shaft 66 is optionally configured in a non-linear shape corresponding to the pathway 52 before or during insertion into the patient. The sheath 68 extends from incision site 130 near where the implantable pulse generator 12 will be implanted to incision site 132 near the therapy delivery element 14. In some examples, the sheath 68 extends from incision site 132. Proximal end 74 of the sheath 68 is accessible at incision site 130 and distal end 72 is accessible near incision site 132. In some examples, the proximal end 74 extends outwardly from the living body from the incision site 130 and the distal end 72 extends outwardly from the living body from the incision site 132. The secondary handle 64 has already been removed.

In one embodiment, the surgeon inserts proximal end 36 of the therapy delivery elements 14 or proximal end 42 of the lead extension 16 (see FIG. 1) into lumen 134 (see FIG. 9) of the sheath 68 through distal end 72. Once the therapy delivery elements 14 are in place, the surgeon then grasps proximal end 74 of the sheath 68 and pulls it from the patient, leaving the therapy delivery elements 14 in the subcutaneous pathway 52. Proximal end 36 or 42 is then electrically coupled to the implantable pulse generator 12, as illustrated in FIG. 3.

In an alternate embodiment, lead extension 16 is inserted into the lumen 134 of the sheath 68 from either end 72, 74.

The surgeon has the option to remove the sheath 68 by pulling either end 72, 74. Once the sheath 68 is removed, distal end 38 of the lead extension 16 attached to the therapy delivery element 14 and the proximal end 42 of the lead extension 16 is attached to the implantable pulse generator 12.

Figure 11:
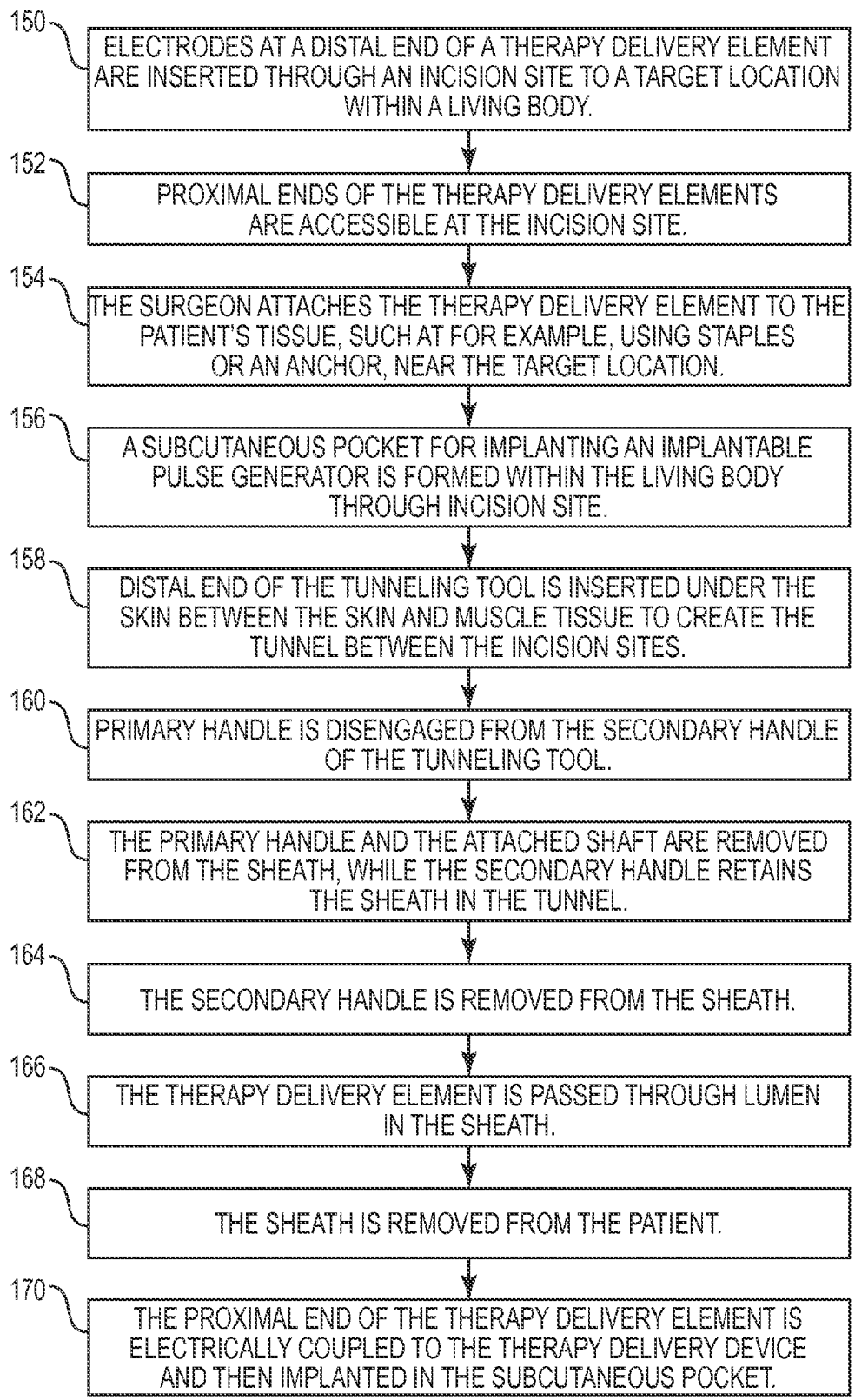
FIG. 11 is a flow diagram of a method of using a tunneling tool in accordance with an embodiment of the present disclosure.

FIG. 11 is a flow diagram of a method of implanting a neurostimulation system within a living body in accordance with an embodiment of the present disclosure. Electrodes 18 at a distal end 44 of a therapy delivery element 14 are inserted through a first incision site 132 to a target location within the living body (150). Proximal ends 36 of the therapy delivery elements 14 are accessible at the incision site 130 (152). The surgeon attaches the therapy delivery element 14 to the patient's tissue, such as for example, using staples or an anchor, near the target location (154). A subcutaneous pocket 54 for implanting an implantable pulse generator 12 is formed within the living body through a second incision site 130 (156). Distal end 70 of the tunneling tool 60 is inserted under the skin between the skin and muscle tissue to create the pathway 52 between the incision sites 130, 132 (158). Primary handle 62 is disengaged from the secondary handle 64 (160). The primary handle 62 and the attached shaft 66 are removed from the sheath 68 while the secondary handle 64 retains the sheath 68 in the pathway 52 (162). The secondary handle 64 is separated from the sheath 68 (164). The therapy delivery element 14 (or an extension thereof) is passed through lumen 134 in the sheath 68 (166). The sheath 68 is then removed from the patient (168). The proximal end 36 of the therapy delivery element 14 is electrically coupled to the implantable pulse generator 12 and the implantable pulse generator 12 is then implanted in the subcutaneous pocket 54 (170).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. A tunneling tool for creating a pathway from a first incision to a second incision for implanting a therapy delivery element in a living body, the tunneling tool comprising:
   an elongated shaft including an outer shaft surface extending from a proximal shaft end to a distal shaft end;
   a sheath including an outer sheath surface defining a lumen slidably positionable over at least a portion of the outer shaft surface;
   a primary handle secured to the proximal shaft end opposite the distal shaft end;
   a secondary handle with an internal secondary handle opening that is larger than the outer shaft surface but smaller than the outer sheath surface at a proximal sheath end, wherein:
      the secondary handle intermediate the primary handle and the sheath is slidable axially along the elongated shaft received in the internal secondary handle opening so that the secondary handle abuts, but is not attachable to the proximal sheath end, wherein the sheath in abutting contact with the secondary handle is unable to move proximally with respect to the secondary handle; and
      the primary handle secured to the elongated shaft is manipulatable in a proximal direction away from the secondary handle to separate the primary and secondary handles from each other to thereby completely remove the elongated shaft secured to the primary handle from within the sheath lumen and then permit manipulation of the secondary handle away from abutting the proximal sheath end, while, at the same time, leaving the sheath within the pathway in the living body to facilitate implanting of the therapy delivery element in the living body; and
   a locking mechanism releasably engaging the secondary handle to the primary handle, the locking mechanism including:

a protrusion formed at a distal end of the primary handle, the protrusion including at least one first recess in the protrusion, the at least one first recess extending radially inwardly from an outer circumferential surface of the protrusion such that the at least one first recess forms a channel within the outer circumferential surface of the protrusion; and a second recess defined by a sidewall of the secondary handle and formed within a proximal end of the secondary handle, the second recess being sized to fit over the protrusion, the second recess including at least one tab extending radially inwardly from an inner circumferential surface of the sidewall of the secondary handle, the at least one tab sized to releasably engage with the at least one first recess in the protrusion in a locked position.

2. The tunneling tool of claim 1, wherein the at least one tab engages with the at least one first recess on the protrusion with a twisting motion.

3. The tunneling tool of claim 1, wherein the elongated shaft comprises a non-linear configuration.

4. The tunneling tool of claim 1, wherein the elongated shaft is configured to be bent into a shape by a surgeon and retain the shape while creating the pathway.

5. The tunneling tool of claim 1, wherein the distal shaft end is blunt to inhibit damage to tissue.

6. The tunneling tool of claim 1, wherein the therapy delivery element includes a lead.

7. A neurostimulation system comprising:
an implantable pulse generator;
a therapy delivery element including a lead, the therapy delivery element comprising a proximal end adapted to electrically couple with the implantable pulse generator and a distal end with an electrode electrically coupled to the implantable pulse generator;
an anchor for securing the therapy delivery element in a desired location within a living body;
a tunneling tool for creating a pathway from a first incision to a second incision for implanting the therapy delivery element in a living body, the tunneling tool comprising:
an elongated shaft including an outer shaft surface extending from a proximal shaft end to a distal shaft end;
a sheath including an outer sheath surface defining a lumen slidably positionable over at least a portion of the outer shaft surface;
a primary handle secured to the proximal shaft end opposite the distal shaft end;
a secondary handle with an internal secondary handle opening that is larger than the outer shaft surface but smaller than the outer sheath surface at a proximal sheath end, wherein:
the secondary handle intermediate the primary handle and the sheath is slidable axially along the elongated shaft received in the internal secondary handle opening so that the secondary handle abuts, but is not attachable to the proximal sheath end, wherein the sheath in abutting contact with the secondary handle is unable to move proximally with respect to the secondary handle; and
the primary handle secured to the elongated shaft is manipulatable in a proximal direction away from the secondary handle to separate the primary and secondary handles from each other to thereby completely remove the elongated shaft secured to the primary handle from within the sheath lumen and then permit manipulation of the secondary handle away from abutting the proximal sheath end, while, at the same time, leaving the sheath within the pathway in the living body to facilitate implanting of the therapy delivery element in the living body; and a locking mechanism releasably engaging the secondary handle to the primary handle, wherein the sheath is retained in a desired location within the living body by retaining the secondary handle relative to the living body, as the primary handle is used to remove the elongated shaft from the sheath, the locking mechanism including:
a protrusion formed at a distal end of the primary handle, the protrusion including at least one first recess in the protrusion, the at least one first recess extending radially inwardly from an outer circumferential surface of the protrusion such that the at least one first recess forms a channel within the outer circumferential surface of the protrusion; and
a second recess defined by a sidewall of the secondary handle and formed within a proximal end of the secondary handle, the second recess being sized to fit over the protrusion, the second recess including at least one tab extending radially inwardly from an inner circumferential surface of the sidewall of the secondary handle, the at least one tab sized to releasably engage with the at least one first recess in the protrusion in a locked position.

8. The neurostimulation system of claim 7, wherein the elongated shaft is configured to be bent into a shape by a surgeon and retain the shape while creating the pathway.

9. The neurostimulation system of claim 7, wherein the distal shaft end is blunt to inhibit damage to tissue.

10. A method of creating a pathway from a first incision to a second incision for implanting a therapy delivery element in a living body, the method comprising:
inserting a distal end of a tunneling tool between skin and muscle tissue in the living body to create the pathway between the skin tissue and the muscle tissue from the first incision to the second incision, the tunneling tool including a shaft including a primary handle at a proximal end of the shaft, a flexible sheath removably disposed on the shaft, and a secondary handle removably disposed on the shaft between the primary handle and the flexible sheath, the secondary handle being engaged with the primary handle;
disengaging the primary handle from the secondary handle of the tunneling tool after inserting the distal end of the tunneling tool between the skin and muscle to create the pathway, the secondary handle abutting, but not attached to, a proximal sheath end of the flexible sheath positioned on the shaft of the tunneling tool, the shaft including an outer shaft surface extending from a proximal shaft end to a distal shaft end, the sheath including an outer sheath surface defining a lumen slidably positionable over at least a portion of the outer shaft surface, the secondary handle including an internal opening that is larger than the outer shaft surface but smaller than the outer sheath surface at the proximal sheath end, wherein the smaller size of the internal opening of the secondary handle prevents the secondary handle from attaching to the proximal sheath end;
holding the secondary handle relative to the living body to secure the flexible sheath located in the pathway, wherein the flexible sheath in abutting contact with the secondary handle is unable to move proximally with respect to the secondary handle;

moving the primary handle proximally relative to the secondary handle after disengaging the primary handle from the secondary handle, the secondary handle, intermediate the primary handle and the sheath, being slidable axially along the shaft received in the internal opening to completely remove the shaft secured to the primary handle of the tunneling tool from the flexible sheath and from the secondary handle, leaving the flexible sheath within the pathway in the living body to facilitate implanting of the therapy delivery element in the living body, wherein the proximal sheath end extends outwardly from the living body from the second incision and the distal sheath end extends outwardly from the living body from the first incision;

separating the secondary handle from abutting the flexible sheath after removing the shaft from within the flexible sheath;

passing the therapy delivery element through the flexible sheath; and removing the flexible sheath from the pathway by pulling one of the proximal sheath end and a distal sheath end.

11. The method of claim 10, comprising disengaging a locking mechanism releasably engaging the secondary handle to the primary handle.

12. The method of claim 10, comprising shaping the shaft before inserting into the living body.

13. The method of claim 10, wherein disengaging the primary handle from the secondary handle includes twisting the secondary handle with respect to the primary handle.

14. The method of claim 10, wherein the proximal sheath end is located in a recess in the secondary handle.

15. The method of claim 10, comprising sliding the internal opening in the secondary handle along the shaft as the shaft is removed from the sheath.

16. The method of claim 10, wherein passing the therapy delivery element through the flexible sheath includes passing a lead through the flexible sheath.

17. The method of claim 10, wherein disengaging the primary handle from the secondary handle includes releasably engaging a locking mechanism, the locking mechanism including:
 a protrusion formed at a distal end of the primary handle, the protrusion including at least one first recess in the protrusion, the at least one first recess extending radially inwardly from an outer circumferential surface of the protrusion such that the at least one first recess forms a channel within the outer circumferential surface of the protrusion; and
 a second recess defined by a sidewall of the secondary handle and formed within a proximal end of the secondary handle, the second recess being sized to fit over the protrusion, the second recess including at least one tab extending radially inwardly from an inner circumferential surface of the sidewall of the secondary handle, the at least one tab sized to releasably engage with the at least one first recess in the protrusion in a locked position.

18. A method of implanting a neurostimulation system within a living body, the method comprising:
 positioning an electrode at a distal end of a therapy delivery element through a first incision site to a target location within the living body;
 accessing a proximal end of the therapy delivery elements at the first incision site;
 attaching the therapy delivery element to the living body;
 forming a subcutaneous pocket for implanting an implantable pulse generator within the living body through a second incision site;
 inserting a distal end of a tunneling tool between skin and muscle tissue in the living body to create the pathway between the skin tissue and the muscle tissue between the first and second incisions, the tunneling tool including a shaft including a primary handle at a proximal end of the shaft, a flexible sheath removably disposed on the shaft, and a secondary handle removably disposed on the shaft between the primary handle and the flexible sheath, the secondary handle being engaged with the primary handle;
 disengaging the primary handle from the secondary handle of the tunneling tool after inserting the distal end of the tunneling tool between the skin and muscle to create the pathway, the secondary handle abutting, but not attached to, a proximal sheath end of the flexible sheath positioned on the shaft of the tunneling tool, the shaft including an outer shaft surface extending from a proximal shaft end to a distal shaft end, the sheath including an outer sheath surface defining a lumen slidably positionable over at least a portion of the outer shaft surface, the secondary handle including an internal opening that is larger than the outer shaft surface but smaller than the outer sheath surface at the proximal sheath end, wherein the smaller size of the internal opening of the secondary handle prevents the secondary handle from attaching to the proximal sheath end;
 holding the secondary handle relative to the living body to secure the flexible sheath along the pathway, wherein the flexible sheath in abutting contact with the secondary handle is unable to move proximally with respect to the secondary handle;
 moving the primary handle proximally relative to the secondary handle after disengaging the primary handle from the secondary handle, the secondary handle, intermediate the primary handle and the sheath, being slidable axially along the shaft received in the internal opening to completely remove the shaft secured to the primary handle of the tunneling tool from the flexible sheath and from the secondary handle, leaving the flexible sheath within the pathway in the living body to facilitate implanting of the therapy delivery element in the living body, wherein the proximal sheath end extends outwardly from the living body from the second incision and the distal sheath end extends outwardly from the living body from the first incision;
 separating the secondary handle from abutting the flexible sheath after removing the shaft from within the flexible sheath;
 passing the therapy delivery element through the flexible sheath;
 removing the flexible sheath from the pathway by pulling one of the proximal sheath end and a distal sheath end; and
 electrically coupling the proximal end of the therapy delivery element to the implantable pulse generator.

19. The method of claim 18, wherein attaching the therapy delivery element to the living body includes attaching a lead to the living body.

20. The method of claim 18, wherein disengaging the primary handle from the secondary handle includes releasably engaging a locking mechanism, the locking mechanism including:
 a protrusion formed at a distal end of the primary handle, the protrusion including at least one first recess in the protrusion, the at least one first recess extending radially inwardly from an outer circumferential surface of the protrusion such that the at least one first recess forms a channel within the outer circumferential surface of the protrusion; and a second recess defined by a sidewall of the secondary handle and formed within a proximal end of the secondary handle, the second recess being sized to fit over the protrusion, the second recess including at least one tab extending radially inwardly from an inner circumferential surface of the sidewall of the secondary handle, the at least one tab sized to releasably engage with the at least one first recess in the protrusion in a locked position.

* * * * *